(12) United States Patent
Lee et al.

(10) Patent No.: US 8,039,535 B2
(45) Date of Patent: *Oct. 18, 2011

(54) FLAME RETARDANT AND IMPACT MODIFIER, METHOD FOR PREPARING THE SAME, AND THERMOPLASTIC RESIN COMPOSITION INCLUDING THE SAME

(75) Inventors: Min Soo Lee, Uiwang-si (KR); Beom Jun Joo, Uiwang-si (KR)

(73) Assignee: Cheil Industries Inc., Gumi-si (KR)

( * ) Notice: Subject to any disclaimer, the term of this patent is extended or adjusted under 35 U.S.C. 154(b) by 60 days.

This patent is subject to a terminal disclaimer.

(21) Appl. No.: 12/496,717

(22) Filed: Jul. 2, 2009

(65) Prior Publication Data
US 2010/0004364 A1 Jan. 7, 2010

(30) Foreign Application Priority Data

Jul. 3, 2008 (KR) ............................... 2008-0064601
Apr. 6, 2009 (KR) ............................... 2009-0029478

(51) Int. Cl.
*C08K 5/523* (2006.01)
(52) U.S. Cl. ........................................ 524/141; 524/140
(58) Field of Classification Search .................. 524/140, 524/141
See application file for complete search history.

(56) References Cited

U.S. PATENT DOCUMENTS

| 3,639,506 | A | | 2/1972 | Haaf |
| 4,492,660 | A | | 1/1985 | Giolito |
| 4,542,170 | A | * | 9/1985 | Hall et al. ..................... 523/179 |
| 6,140,399 | A | | 10/2000 | Munro |
| 2010/0152345 | A1 | | 6/2010 | Lee et al. |

FOREIGN PATENT DOCUMENTS

| EP | 0728811 A2 | 8/1996 |
| EP | 0970997 A2 | 1/2000 |

OTHER PUBLICATIONS

European Search Report in counterpart European Application No. 09164538.2, dated Oct. 5, 2009.
Anonymous, "Phosphoric acid 2, 4-bis (1, 1-dimethylethyl)phenyl diphenyl ester", Database Registry, Jun. 18, 2008.
European Patent Office Intention to Grant in counterpart European Application No. 09164538 dated Nov. 2, 2010, pp. 1-4.
Office Action in commonly owned U.S. Appl. No. 12/632,862 dated Oct. 26, 2010, pp. 1-5.

* cited by examiner

*Primary Examiner* — Peter Szekely
(74) *Attorney, Agent, or Firm* — Summa, Additon & Ashe, P.A.

(57) ABSTRACT

Disclosed herein is a flame retardant and impact modifier represented by the following Chemical Formula 1. The flame retardant and impact modifier may improve heat resistance and flowability as well as flame retardancy and impact strength of a thermoplastic resin composition. The present invention also provides a method of preparing the foregoing flame retardant and impact modifier and a thermoplastic resin composition including the flame retardant and impact modifier.

[Chemical Formula 1]

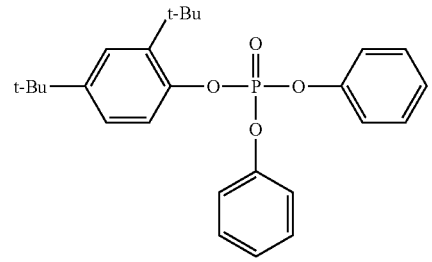

18 Claims, 1 Drawing Sheet

FLAME RETARDANT AND IMPACT MODIFIER, METHOD FOR PREPARING THE SAME, AND THERMOPLASTIC RESIN COMPOSITION INCLUDING THE SAME

CROSS-REFERENCE TO RELATED APPLICATIONS

This non-provisional application claims priority under 35 USC Section 119 from Korean Patent Application No. 2008-64601, filed Jul. 3, 2008, and Korean Patent Application No. 2009-29478, filed Apr. 6, 2009, each of which is hereby incorporated by reference in its entirety.

FIELD OF THE INVENTION

The present invention relates to a flame retardant and impact modifier, method for preparing the same and thermoplastic resin composition including the same.

BACKGROUND OF THE INVENTION

Generally, thermoplastic resins can have good mold processability and mechanical properties and have accordingly been widely used in the production of many electronic goods. However, thermoplastic resins can readily ignite and combust and have significantly no resistance against fire. Thus, thermoplastic resins can readily spread fire from an external ignition source. Accordingly, thermoplastic resins are subject to various mandatory controls on flammability for safety reasons in many countries, and are required to have high flame retardancy to meet the Underwriter's Laboratories Standard for use in electric appliances.

One well known and widely used method for imparting flame retardancy to thermoplastic resins is to add halogen-containing flame retardants and antimony compounds to thermoplastic resin. Such halogen-containing compounds include polybromodiphenyl ether, tetrabromobisphenol A, bromine-substituted epoxy compounds, chlorinated polyethylene and the like. Antimony trioxide and antimony pentoxide are mainly used as the antimony compounds.

Methods for improving the flame-retardant properties of resins using a halogen- and antimony-containing compound can be advantageous because these compounds can readily impart a desired degree of flame-retardancy to the product at a low cost. Accordingly, halogen- and antimony-containing compound have been widely used as flame retardants in the production of many electric goods, office equipment, and materials such as ABS resin, PS, PBT, PET, epoxy resin and the like.

However, halogen-containing compounds can release hydrogen halide gases during molding processes, which can have a harmful effect on health. Further, the halogen- and antimony-containing compounds are unable to decompose under normal circumstances and are insoluble in water, causing the compounds to reside in the atmosphere and to accumulate in the body. In particular, polybromodiphenyl ether, which is the halogen-containing flame retardant primarily used, can produce very toxic gas such as dioxin or furan. Hence, a method for imparting flame retardancy without using halogen-containing compounds has become a matter of concern.

Rubber-modified styrenic resins generally have little remaining char during combustion, and thus it is hard to impart flame retardancy to such resins in their solid state (*Journal of Applied Polymer Science*, 1998, vol. 68, p. 106. Therefore, it is necessary to add a char forming agent to a rubber-modified styrenic resin so that char can be well formed in order to obtain desirable flame retardancy.

A well known and widely used method of imparting flame retardancy without using halogen-containing flame retardants uses a phosphate ester flame retardant. However, relatively high amounts of phosphate ester flame retardants or flame retardant aids are required to obtain sufficient flame retardancy.

U.S. Pat. No. 3,639,506 is directed to a resin composition that acquires flame retardancy by adding a triphenyl phosphate as a flame retardant to a polyphenylene ether resin and a styrenic resin. However, these resin compositions including triphenyl phosphate exhibit a "juicing phenomenon" during molding processes due to the low thermal decomposition temperature of triphenyl phosphate.

SUMMARY OF THE INVENTION

The present invention is directed to a specifically substituted phosphate compound that can be useful as a flame retardant and impact modifier for a thermoplastic resin composition. The flame retardant and impact modifier of the present invention also can be environmentally friendly and does not generate hydrogen halide gases which cause environmental pollution.

The present invention also provides a thermoplastic resin composition including the flame retardant and impact modifier of the invention. The thermoplastic resin composition of the invention can exhibit a good balance of properties such as good heat resistance and flowability as well as high flame retardancy and impact strength. Further, the thermoplastic resin composition including the flame retardant and impact modifier of the present invention may not exhibit the juicing phenomenon when the resin composition is molded.

Accordingly, an aspect of the present invention provides a phosphate compound having a specific substituent. The phosphate compound can be used as a flame retardant and impact modifier. The phosphate compound can be represented by the following Chemical Formula 1:

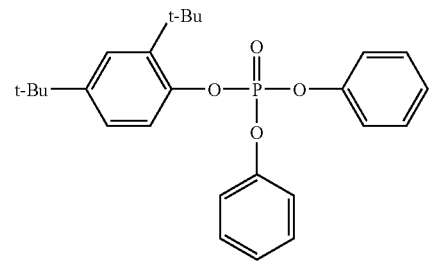

[Chemical Formula 1]

In exemplary embodiments of the invention, the modifier can be prepared by dehydrochloric acid reaction of phosphorus oxychloride and 2,4-di-tert-butylphenol in the presence of metal catalyst to provide 2,4-di-tert-butylphenyl dichlorophosphate. The 2,4-di-tert-butylphenyl dichlorophosphate can then be reacted with phenol to provide the phosphate compound of Formula I.

Another aspect of the present invention relates to a novel method for preparing the foregoing flame retardant and impact modifier. In exemplary embodiments, the method comprises reacting a phosphorus oxychloride with 2,4-di-tert-butylphenol to prepare 2,4-di-tert-butylphenyl dichlorophosphate; and reacting 2,4-di-tert-butylphenyl dichlorophosphate with phenol to provide the phosphate compound of Formula I.

In exemplary embodiments of the invention, an equivalent of 2,4-di-tert-butylphenol is reacted with about 3 to about 6 equivalents of phosphorus oxychloride. In exemplary embodiments, an equivalent of 2,4-di-tert-butylphenyl dichlorophosphate is reacted with about 2 to about 4 equivalents of phenol.

Another aspect of the invention provides a thermoplastic resin composition containing the foregoing flame retardant and impact modifier. In exemplary embodiments of the invention, the resin composition may comprise about 100 parts by weight of a thermoplastic resin; and about 0.1 to about 30 parts by weight of the foregoing flame retardant and impact modifier.

In exemplary embodiments of the invention, the thermoplastic resin may be polystyrene, styrene-acrylonitrile copolymer resin (SAN), rubber modified polystyrene resin (HIPS), rubber modified aromatic vinyl copolymer resin, ASA resin, MABS resin, polycarbonate resin, polyphenylene ether resin, polyphenylene sulfide resin, polyester resin, polyolefin resin, poly(meth)acrylate resin, polyamide resin, polyvinyl chloride resin and the like. These thermoplastic resins may be used alone or in combination with one another.

In exemplary embodiments of the invention, the thermoplastic resin may comprise about 70 to about 99% by weight of a rubber modified polystyrene and about 1 to about 30% by weight of a polyphenylene ether resin. The resin composition may have a flame retardancy of V-1 or V-0 measured in accordance with UL 94 using a ⅛" thick test specimen and an impact strength of about 10 to about 50 kgf·cm/cm measured in accordance with ASTM D 256 using a ⅛" notched thick test specimen.

In another exemplary embodiment of the invention, the thermoplastic resin may be polycarbonate resin. The resin composition may have a flame retardancy of V-0 measured in accordance with UL 94 using a ⅛" thick test specimen and an impact strength of about 58 to about 80 kgf·cm/cm measured in accordance with ASTM D 256 using a ⅛" notched thick test specimen.

In another exemplary embodiment of the invention, the thermoplastic resin comprises about 55 to about 90% by weight of a polycarbonate resin and about 10 to about 45% by weight of a rubber modified aromatic vinyl copolymer resin. The resin composition may have a flame retardancy of V-1 or V-0 measured in accordance with UL 94 using a ⅛" thick test specimen and an impact strength of about 55 to about 70 kgf·cm/cm measured in accordance with ASTM D 256 using a ⅛" notched thick test specimen.

In another exemplary embodiment of the invention, the thermoplastic resin may further include additives such as heat stabilizers, lubricants, releasing agents, plasticizers, antistatic agents, flame retardant aids, anti-dripping agents, antioxidants, compatibilizers, light stabilizers, pigments, dyes, inorganic fillers and the like. These additives may be used alone or in combination with one another. A more detailed description of each of the components of the resin composition according to various embodiments follows.

DETAILED DESCRIPTION OF THE INVENTION

Figure 1:
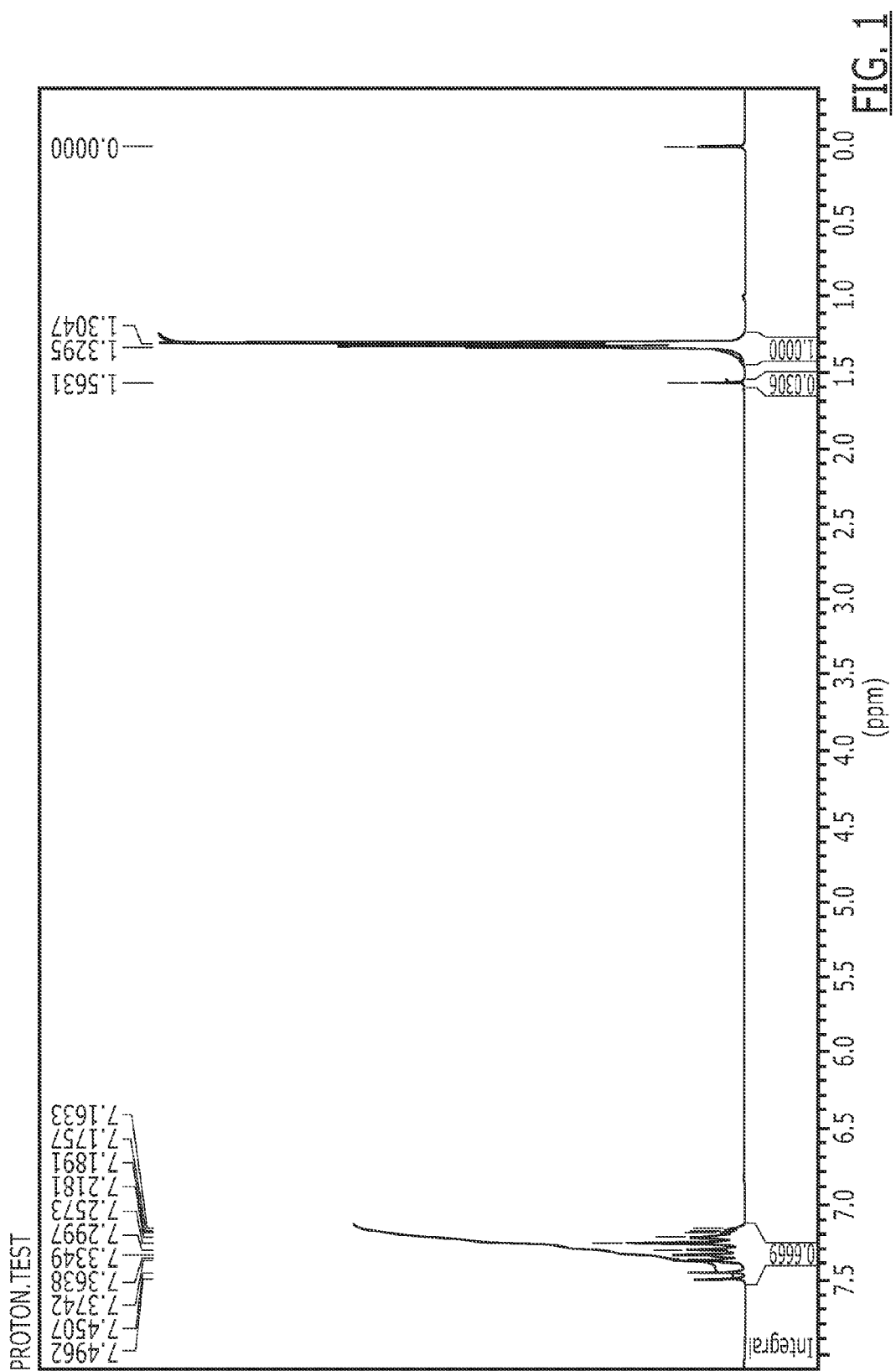
FIG. 1 shows a ¹H-NMR spectrum of 2,4-di-tert-butylphenyl diphenylphosphate.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

2,4-Di-Tert-Butylphenyl Diphenylphosphate and Method For Preparing the Same

The phosphate compound of the invention is a triphenyl phosphate in which one of the phenyl groups bears tert-butyl groups on specific sites as illustrated in the following Chemical Formula 1:

[Chemical Formula 1]

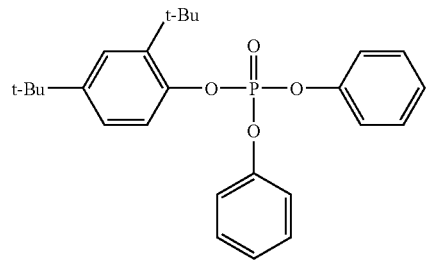

Triphenyl phosphate is a well known flame retardant. However, triphenyl phosphate cannot provide sufficient flame retardancy. As a result, a large amount of triphenyl phosphate is typically added to a resin composition to obtain sufficient flame retardancy. Large amounts of triphenyl phosphate, however, can cause the juicing phenomenon during molding processes and also decrease impact resistance. The flame retardant and impact modifier of the invention may significantly improve not only flame retardancy but also impact strength and may provide a good balance of properties by introducing tert-butyl groups at specific sites on one of the phenyl groups of triphenyl phosphate.

If other alkyl groups such as methyl group, ethyl group, propyl group, or n-butyl group are introduced instead of the tert-butyl group, it may be difficult to obtain good flame retardancy and may cause volatilization of the flame retardant during molding processes.

Further, if the tert-butyl groups are present at position 3,4-, position 2,6- or position 2,4,6- on the phenyl group of triphenyl phosphate, the compound can be difficult to synthesize, thereby complicating the process and increasing cost.

In exemplary embodiments of the invention, the modifier can be prepared by dehydrochloric acid reaction of phosphorus oxychloride and 2,4-di-tert-butylphenol in the presence of metal catalyst to provide a 2,4-di-tert-butylphenyl dichlorophosphate intermediate. Examples of the metal catalysts may include, but are not limited to, metal chlorides such as magnesium chloride, aluminum chloride, calcium chloride and the like, and combinations thereof. The 2,4-di-tert-butylphenyl dichlorophosphate can then be reacted with phenol to provide the compound of Formula I.

In exemplary embodiments of the invention, 2,4-di-tert-butylphenyl diphenylphosphate can be prepared by reacting a phosphorus oxychloride with 2,4-di-tert-butylphenol to prepare 2,4-di-tert-butylphenyl dichlorophosphate; and reacting the 2,4-di-tert-butylphenyl dichlorophosphate with phenol.

In exemplary embodiments of the invention, an equivalent of 2,4-di-tert-butylphenol is reacted with about 3 to about 6, for example about 4 to about 5, equivalents of phosphorus oxychloride. Within these ranges, the degree of reaction completion can be increased while reducing side products. In other exemplary embodiments, an equivalent of 2,4-di-tert-butylphenol can be reacted with about 3.5 to about 5.5 equivalents of phosphorus oxychloride. In yet other exemplary embodiments, an equivalent of 2,4-di-tert-butylphenol can be reacted with about 4.5 to about 5.5 equivalents of phosphorus oxychloride.

The reaction of phosphorus oxychloride and 2,4-di-tert-butylphenol may be conducted at a temperature of about 80 to about 160° C., for example about 100 to about 150° C. Further, the reaction can be carried out in the presence of a metal catalyst under a nitrogen atmosphere. Examples of the metal catalysts may include, but are not limited to, metal chlorides such as magnesium chloride, aluminum chloride, calcium chloride and the like, and combinations thereof. In exemplary embodiments of the invention, an equivalent of 2,4-di-tert-butylphenol is reacted with about 0.01 to about 10, for example about 0.01 to about 5, equivalents of the metal catalyst. These ranges can minimize impurities and can be cost effective. The reaction time may be about 4 to about 15 hours, for example about 5 to about 10 hours. In exemplary embodiments of the invention, reaction time may be about 5.5 to about 8 hours.

After the reaction of phosphorus oxychloride with 2,4-di-tert-butylphenol, 2,4-di-tert-butylphenyl dichlorophosphate in the liquid state can be obtained as an intermediate. Phenol can be added to the 2,4-di-tert-butylphenyl dichlorophosphate to initiate a reaction. In exemplary embodiments of the invention, an equivalent of 2,4-di-tert-butylphenyl dichlorophosphate can be reacted with about 2 to about 4 equivalents of phenol. Within these ranges, the degree of reaction completion can be increased while reducing side products. In exemplary embodiments, an equivalent of 2,4-di-tert-butylphenyl dichlorophosphate can be reacted with about 2 to about 3.5 equivalents of phenol. In other embodiments, an equivalent of 2,4-di-tert-butylphenyl dichlorophosphate can be reacted with about 3 to about 4 equivalents of phenol.

If necessary, a reaction solvent may be used along with the phenol. The reaction solvent may include without limitation benzene, toluene, xylene, 1,4-dioxane, methylene chloride, ethylene chloride and the like. These reaction solvents can be used alone or in combination.

2,4-di-tert-butylphenyl dichlorophosphate and phenol can be reacted at about 100 to about 130° C. for about 4 to about 10 hours with stirring to obtain 2,4-di-tert-butylphenyl diphenylphosphate in the liquid state. In exemplary embodiments, the reaction of 2,4-di-tert-butylphenyl dichlorophosphate and phenol can be carried out at about 110 to about 130° C. for about 4.5 to about 7.5 hours.

In exemplary embodiments of the invention, the method may further comprise cooling to a temperature of about 0 to about 40° C., for example about 10 to about 30° C. after the reaction.

In exemplary embodiments of the invention, the 2,4-di-tert-butylphenyl diphenylphosphate thus obtained can be subjected to filtering and drying processes. In exemplary embodiments, the reaction product can be filtered, dried and washed followed by further drying in a vacuum oven, thereby obtaining phosphate compound represented by the above Chemical Formula 1 with about 85 to about 99% yield.

Thermoplastic Resin Composition

Another aspect of the invention provides a thermoplastic resin composition comprising the foregoing flame retardant and impact modifier.

In exemplary embodiments of the invention, the resin composition comprises about 100 parts by weight of thermoplastic resin and about 0.1 to about 30 parts by weight of the flame retardant and impact modifier.

The thermoplastic resin may be polystyrene, styrene-acrylonitrile copolymer resin (SAN), rubber modified polystyrene resin (HIPS), rubber modified aromatic vinyl copolymer resin, ASA resin, MABS resin, polycarbonate resin, polyphenylene ether resin, polyphenylene sulfide resin, polyester resin, polyolefin resin, poly(meth)acrylate resin, polyamide resin, polyvinyl chloride resin and the like. These thermoplastic resins may be used alone or in combination with one another.

In exemplary embodiments of the invention, the thermoplastic resin may comprise about 70 to about 99% by weight of a rubber modified polystyrene and about 1 to about 30% by weight of a polyphenylene ether resin.

The rubber modified polystyrene resin may be prepared by polymerizing rubbery polymer and a styrenic monomer.

Examples of the rubbery polymers may include, but are not limited to, diene rubbers such as polybutadiene, poly(styrene-butadiene), poly(acrylonitrile-butadiene), and the like; saturated rubbers in which hydrogen is added to a diene rubber; isoprene rubbers; acrylic based rubbers including alkyl acrylates such as polybutyl acrylate; and terpolymers of ethylene-propylene-diene (EPDM), and the like, and combinations thereof. Polybutadiene, poly(styrene-butadiene), isoprene rubbers and alkyl acrylates can be used.

In exemplary embodiments of the invention, the rubbery polymer may be used in an amount of about 3 to about 30 wt % based on total weight of the rubber modified polystyrene resin, for example about 5 to about 15 wt %. The rubbery polymer can have a particle size of about 0.1 to about 4.0 μm. In exemplary embodiments, the rubbery polymer may be dispersed in the form of bi-modal or tri-modal.

Examples of the styrenic monomer may include without limitation styrene, α-methyl styrene, β-methyl styrene, p-methyl styrene, p-t-butyl styrene, ethyl styrene, and the like, and combinations thereof. These styrenic monomers can be used in an amount of about 70 to about 97% by weight based on total weight of the rubber modified polystyrene resin, for example about 85 to about 95% by weight.

The rubber modified polystyrene resin may also include other monomers such as but not limited to acrylonitrile, acrylic acid, methacrylic acid, maleic acid anhydride, N-substituted maleimide, and the like, and combinations thereof, in order to impart properties such as chemical resistance, processability and heat resistance. These monomers may be used in an amount of about 40% by weight or less based on total weight of the rubber modified polystyrene resin.

The rubber modified polystyrene resin can be polymerized with heat and with no polymerization initiator, although a polymerization initiator can optionally be also used. The polymerization initiators may include without limitation organic peroxides such as benzoyl peroxide, t-butyl hydroperoxide, acetyl peroxide and cumene hydroperoxide or azo compounds such as azobisisobutyronitrile, and the like. The polymerization initiators can be used alone or in combination therewith.

The rubber modified polystyrene resin can be prepared using known polymerization methods, such as bulk polymerization, suspension polymerization, emulsion polymerization, or a combination thereof.

The polyethylene ether resin may be employed to improve flame retardancy and heat resistance Examples of suitable polyphenylene ether resins can include without limitation poly(2,6-dimethyl-1,4-phenylene) ether, poly(2,6-diethyl-1,4-phenylene) ether, poly(2,6-dipropyl-1,4-phenylene) ether, poly(2-methyl-6-ethyl-1,4-phenylene) ether, poly(2-methyl- 6-propyl-1,4-phenylene) ether, poly(2-ethyl-6-propyl-1,4-phenylene) ether, poly(2,6-diphenyl-1,4-phenylene) ether, copolymer of poly(2,6-dimethyl-1,4-phenylene) ether and poly(2,3,6-trimethyl-1,4-phenylene) ether, copolymer of poly(2,6-dimethyl-1,4-phenylene) ether, poly(2,3,5-triethyl-1,4-phenylene) ether, and the like, and combinations thereof. The degree of polymerization of the polyphenylene ether is not limited specifically, but can vary depending on factors such as heat-stability or processability of the resin composition. The viscosity of the polyphenylene ether can be in the range of about 0.2 to about 0.8 measured in chloroform solvent at 25° C.

According to the present invention, the polyphenylene ether may be used in an amount of about 1 to about 30% by weight. Within this range, good flame retardancy, heat stability and processability can be obtained. In another exemplary embodiment, the polyphenylene ether may be used in an amount of about 15 to about 30% by weight.

When the base resin is a blend of 70 to about 99% by weight of a rubber modified polystyrene and about 1 to about 30% by weight of a polyphenylene ether resin, the flame retardant and impact modifier may be used in an amount of about 10 to about 30 parts by weight, for example about 15 to about 25 parts by weight based on about 100 parts by weight of the base resin. The resin composition using the blend of a rubber modified polystyrene and polyphenylene ether resin as a base resin may have a flame retardancy of V-1 or V-0 measured in accordance with UL 94 using a 1/8" thick test specimen and an impact strength of about 10 to about 50 kgf·cm/cm measured in accordance with ASTM D 256 using a 1/8" notched thick test specimen.

In some embodiments, the thermoplastic resin may be a polycarbonate resin. The polycarbonate resin may have a weight average molecular weight of about 10,000 to about 500,000 g/mol, for example about 15,000 to about 100,000 g/mol. Within this range, a good balance of mechanical properties and moldability can be obtained.

The polycarbonate resin may include without limitation linear polycarbonate resin, branched polycarbonate resin, polyester carbonate copolymer resin, and combinations thereof.

When the polycarbonate resin is used as a base resin, the flame retardant and impact modifier may be used in an amount of about 1 to about 15 parts by weight, for example about 3 to about 10 parts by weight based on about 100 parts by weight of the base resin. The resin composition containing polycarbonate resin as a base resin may have a flame retardancy of V-0 measured in accordance with UL 94 using a 1/8" thick test specimen and an impact strength of about 58 to about 80 kgf·cm/cm measured in accordance with ASTM D 256 using a 1/8" notched thick test specimen.

In some embodiments, the thermoplastic resin may comprise about 55 to about 90% by weight of a polycarbonate resin and about 10 to about 45% by weight of a rubber modified aromatic vinyl copolymer resin.

In exemplary embodiments of the invention, the rubber modified aromatic vinyl copolymer resin may comprise about 20 to about 50% by weight of a rubbery polymer unit, about 40 to about 60% by weight of an aromatic vinyl unit and about 10 to about 30% by weight of a cyanide vinyl unit.

Examples of the rubbery polymers may include, but are not limited to, diene rubbers such as polybutadiene, poly(styrene-butadiene), poly(acrylonitrile-butadiene), and the like; saturated rubbers in which hydrogen is added to a diene rubber; isoprene rubbers; acrylic based rubbers including alkyl acrylates such as polybutyl acrylate; and terpolymers of ethylene-propylene-diene (EPDM), and the like, and combinations thereof. The average size of the rubber particles can range from about 0.1 to about 4 µm taking into account the desired impact strength and appearance of the resin composition.

Examples of the aromatic vinyl unit may include without limitation styrene, α-methyl styrene, β-methyl styrene, p-methyl styrene, p-t-butyl styrene, ethyl styrene, vinyl xylene, monochlorostyrene, dichlorostyrene, dibromostyrene, vinyl naphthalene, and the like, and combinations thereof. These aromatic vinyl monomers can be used alone or in combination with one another.

Examples of the cyanide vinyl unit may include without limitation acrylonitrile, ethacrylonitrile, methacrylonitrile, and the like, and combinations thereof.

The rubber modified aromatic vinyl copolymer resin may also include other monomers such as but not limited to acrylic acid, methacrylic acid, maleic acid anhydride, N-substituted maleimide, and the like, and combinations thereof, in order to impart good processability and heat resistance.

When the base resin comprising about 55 to about 90% by weight of a polycarbonate resin and about 10 to about 45% by weight of a rubber modified aromatic vinyl copolymer resin is used, the flame retardant and impact modifier may be used in an amount of about 15 to about 30 parts by weight, for example about 20 to about 25 parts by weight based on about 100 parts by weight of the base resin. The resin composition containing the above base resin may have a flame retardancy of V-1 or V-0 measured in accordance with UL 94 using a 1/8" thick test specimen and an impact strength of about 55 to about 70 kgf·cm/cm measured in accordance with ASTM D 256 using a 1/8" notched thick test specimen.

Examples of the polyolefin resin may include without limitation polyethylene resin, polypropylene resin and the like, and combinations thereof. When the polyolefin resin is used as a base resin, the flame retardant and impact modifier may be used in an amount of about 1 to about 20 parts by weight, for example about 3 to about 15 parts by weight based on about 100 parts by weight of the base resin.

Examples of the polyester may include without limitation polyethylene terephthalate (PET), polybutylene terephthalate (PBT) and the like, and combinations thereof. When the polyester resin is used as a base resin, the flame retardant and impact modifier may be used in an amount of about 5 to about 25 parts by weight, for example about 10 to about 20 parts by weight based on about 100 parts by weight of the base resin.

The resin composition according to the present invention may further include other additives. Examples of such additives may include without limitation heat stabilizers, lubricants, releasing agents, plasticizers, antistatic agents, flame retardant aids, anti-dripping agents, anti-oxidants, compatibilizers, light stabilizers, pigments, dyes, inorganic fillers and the like. The additives can be used alone or in combination with one another. Examples of the inorganic fillers may include asbestos, glass fibers, talc, ceramics, sulfates and the like. The additives can be added in an amount of about 30 parts by weight or less based on the total weight of the resin composition.

The resin composition of the present invention may be prepared by conventional methods. For example, the aforementioned components and other additives may be mixed together in a mixer and the mixture may be melt-extruded through a conventional extruder into a pellet form. The resin pellets may be used to prepare plastic molded articles by various molding process such as injection, extrusion, vacuum molding or casting molding.

Another aspect of the invention provides a molded article molded from the foregoing resin composition. Since the molded article has excellent impact resistance, flowability, flame retardancy and heat stability and does not exhibit a juicing phenomenon, it is well suitable for parts of electric/electronic goods, housings, parts of automobiles, convenience goods, structural materials, and the like.

The invention may be better understood by reference to the following examples which are intended for the purpose of illustration and are not to be construed as in any way limiting the scope of the present invention, which is defined in the claims appended hereto.

EXAMPLES

Preparative Example

Preparation of a 2,4-di-tert-butylphenyl diphenylphosphate

Phosphorus oxychloride (767 g, 5.0 mol), 2,4-di-tert-butylphenol (206 g, 1 mol) and magnesium chloride (1 g, 0.01 mol) are charged into a vessel, and stirred at 130° C. for 6 hours under a nitrogen atmosphere. The temperature of the vessel is cooled to 90° C. while phosphorus oxychloride residue is recovered under a reduced pressure and then phenol (188 g, 2 mol) and toluene (1 L) are charged into the vessel and stirred at 130° C. for 5 hours under a nitrogen atmosphere. After the completion of the reaction, the temperature of the vessel is lowered to room temperature and water (1 L) is added to the vessel and stirred. Then the organic layer was taken and distilled under reduced pressure to obtain 2,4-di-tert-butylphenyl diphenylphosphate with 98% or more purity and 95% yield.

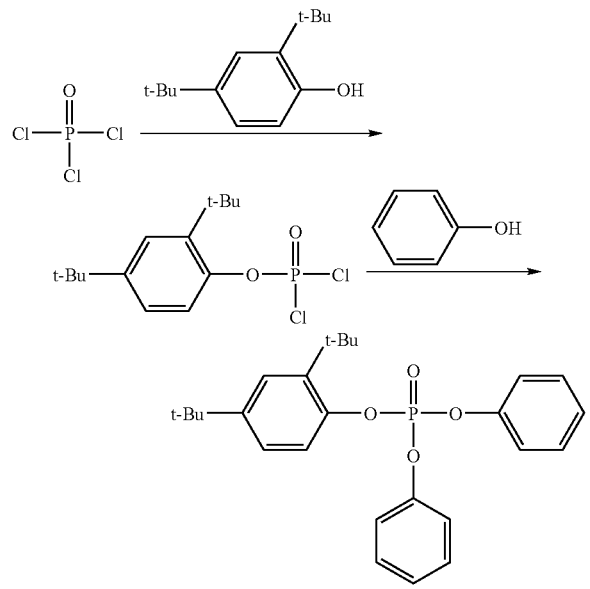

Example 1

To a blend of 75 parts by weight of rubber modified polystyrene resin (HIPS, HG-1760S manufactured by Cheil Industries Inc.) and 25 parts by weight of poly(2,6-dimethylphenylether) manufactured by Mitsubishi Engineering-Plastics Corp. of Japan (product name: PX-100F) is added 2,4-di-tert-butylphenyl diphenylphosphate prepared from the above preparative example in a ratio as shown in Table 1 to extrude through a conventional twin screw extruder at a temperature range of 200-280° C. into pellets. The resin pellets are dried at 80° C. for 2 hours, and molded into test specimens using a injection molding machine at 180-280° C. with a mold temperature of 40-80° C. The flame retardancy is measured in accordance with UL94 VB at a thickness of 1/8". The Izod impact strength is measured in accordance with ASTM D-256 at a thickness of 1/8" (kgf·cm/cm).

Examples 2-3

Examples 2-3 are conducted in the same manner as in the Example 1 above except that polycarbonate resin (product name: Panlite L-1225 Grade manufactured by Teijin Company of Japan) is used as a base resin and that 2,4-di-tert-butylphenyl diphenylphosphate is used in a different amount.

Example 4

Example 4 is conducted in the same manner as in the Example 1 above except that a blend of polycarbonate resin (product name: Panlite L-1225 Grade manufactured by Teijin Company of Japan) and ABS (g-ABS/SAN=3/7) is used as a base resin and that 2,4-di-tert-butylphenyl diphenylphosphate is used in a different amount. The g-ABS is manufactured by Cheil Industries Inc. with a product name of CHT. The SAN is manufactured by Cheil Industries Inc. with a product name of AP-70.

Comparative Examples 1-4

Comparative Examples 1-4 are conducted in the same manner as in the Examples above except that triphenyl phosphate manufactured by Daihachi Chemical Industry Co., Ltd. is used as a flame retardant instead of 2,4-di-tert-butylphenyl diphenylphosphate with a different amount.

The results are shown in Table 1.

TABLE 1

|  | Examples | | | | Comparative Examples | | | |
| --- | --- | --- | --- | --- | --- | --- | --- | --- |
|  | 1 | 2 | 3 | 4 | 1 | 2 | 3 | 4 |
| HIPS | 75 | — | — | — | 75 | 75 | — | — |
| PPE | 25 | — | — | — | 25 | 25 | — | — |
| PC | — | 100 | 100 | 60 | — | — | 100 | 60 |
| ABS | — | — | — | 40 | — | — | — | 40 |
| 2,4-di-tert-butylphenyl diphenylphosphate | 20 | 3 | 5 | 18 | — | — | — | — |
| Triphenyl phosphate | — | — | — | — | 10 | 20 | 3 | 18 |

TABLE 1-continued

|  | Examples | | | | Comparative Examples | | | |
| --- | --- | --- | --- | --- | --- | --- | --- | --- |
|  | 1 | 2 | 3 | 4 | 1 | 2 | 3 | 4 |
| 2,4,6-trimethyl phenyl diphenylphosphate | — | — | — | — | — | — | — | — |
| UL94 (⅛") | V-1 | V-0 | V-0 | V-1 | Fail | Fail | V-1 | Fail |
| first average combustion time (sec) | 8.2 | 0.6 | 1.0 | 4.4 | ≧40.0 | 14.5 | 11.5 | 4.6 |
| second average combustion time (sec) | 15.2 | 5.8 | 3.1 | 20.3 | — | 41.5 | 5.0 | ≧40.0 |
| IZOD | 10.5 | 61.2 | 59.8 | 55.6 | 7.5 | 7.4 | 60.9 | 54.8 |

As shown in Table 1, it can be seen that the Examples employing 2,4-di-tert-butylphenyl diphenylphosphate exhibit good flame retardancy and impact strength, as compared to the Comparative Examples using triphenyl phosphate.

Comparative Examples 5-8

Comparative Examples 5-8 are conducted in the same manner as in the above Examples above except that 2,4,6-trimethyl phenyl diphenylphosphate is used as a flame retardant instead of 2,4-di-tert-butylphenyl diphenylphosphate. The results of comparative Examples 5-8 are shown in Table 2.

TABLE 2

|  | Comparative Examples | | | |
| --- | --- | --- | --- | --- |
|  | 5 | 6 | 7 | 8 |
| HIPS | 75 | — | — | — |
| PPE | 25 | — | — | — |
| PC | — | 100 | 100 | 60 |
| ABS | — | — | — | 40 |
| 2,4-di-tert-butylphenyl diphenylphosphate | — | — | — | — |
| Triphenyl phosphate | — | — | — | — |
| 2,4,6-trimethyl phenyl diphenylphosphate | 20 | 3 | 5 | 18 |
| UL94 flame retardancy (⅛") | Fail | V-0 | V-0 | Fail |
| first average combustion time (sec) | 15.2 | 0.6 | 1.0 | 6.8 |
| second average combustion time (sec) | 20.3 | 6.2 | 5.4 | 25.3 |
| IZOD | 9.5 | 58.6 | 57.4 | 52.6 |

As shown in Table 2, it can be seen that the Examples employing 2,4-di-tert-butylphenyl diphenylphosphate exhibit good flame retardancy and impact strength, as compared to the Comparative Examples using 2,4,6-trimethyl phenyl diphenylphosphate.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A method of preparing a flame retardant and impact modifier comprising:
   reacting a phosphorus oxychloride with 2,4-di-tert-butylphenol to prepare 2,4-di-tert-butylphenyl dichlorophosphate; and
   reacting 2,4-di-tert-butylphenyl dichlorophosphate with phenol to prepare a flame retardant and impact modifier of the following Chemical Formula 1:

[Chemical Formula 1]

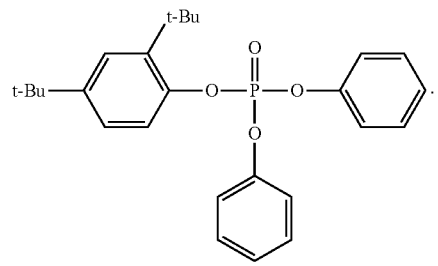

2. The method of claim 1, wherein an equivalent of 2,4-di-tert-butylphenol is reacted with about 3 to about 6 equivalents of phosphorus oxychloride.

3. The method of claim 1, wherein an equivalent of 2,4-di-tert-butylphenyl dichlorophosphate is reacted with about 2 to about 4 equivalents of phenol.

4. A thermoplastic resin composition comprising:
   about 100 parts by weight of a thermoplastic resin comprising polystyrene, styrene-acrylonitrile copolymer resin (SAN), rubber modified polystyrene resin (HIPS), rubber modified aromatic vinyl copolymer resin, ASA resin, MABS resin, polycarbonate resin, polyphenylene ether resin, polyphenylene sulfide resin, polyester resin, polyolefin resin, poly(meth)acrylate resin, polyamide resin, polyvinyl chloride resin, or a combination thereof; and
   about 0.1 to about 30 parts by weight of a flame retardant and impact modifier represented by the following Chemical Formula 1:

[Chemical Formula 1]

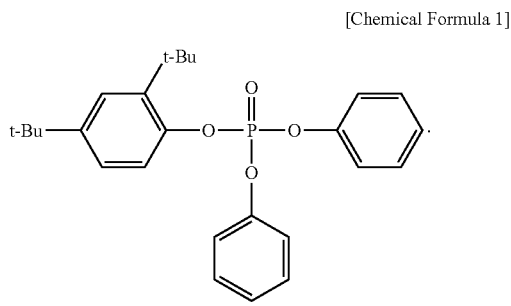

5. The thermoplastic resin composition of claim 4, wherein said thermoplastic resin comprises about 70 to about 99% by weight of a rubber modified polystyrene and about 1 to about 30% by weight of a polyphenylene ether resin.

6. The thermoplastic resin composition of claim 5, wherein said resin composition has a flame retardancy of V-1 or V-0 measured in accordance with UL 94 using a ⅛" thick test specimen and an impact strength of about 10 to about 50 kgf·cm/cm measured in accordance with ASTM D 256 using a ⅛" notched thick test specimen.

7. The thermoplastic resin composition of claim 4, wherein said thermoplastic resin is polycarbonate resin.

8. The thermoplastic resin composition of claim 7, wherein said resin composition has a flame retardancy of V-0 measured in accordance with UL 94 using a ⅛" thick test specimen and an impact strength of about 58 to about 80 kgf·cm/cm measured in accordance with ASTM D 256 using a ⅛" notched thick test specimen.

9. The thermoplastic resin composition of claim 4, wherein said thermoplastic resin comprises about 55 to about 90% by weight of a polycarbonate resin and about 10 to about 45% by weight of a rubber modified aromatic vinyl copolymer resin.

10. The thermoplastic resin composition of claim 9, wherein said resin composition has a flame retardancy of V-1 or V-0 measured in accordance with UL 94 using a ⅛" thick test specimen and an impact strength of about 55 to about 70 kgf·cm/cm measured in accordance with ASTM D 256 using a ⅛" notched thick test specimen.

11. The thermoplastic resin composition of claim 4, further comprising at least one additive selected from heat stabilizers, lubricants, releasing agents, plasticizers, antistatic agents, flame retardant aids, anti-dripping agents, anti-oxidants, compatibilizers, light stabilizers, pigments, dyes, inorganic fillers and combinations thereof.

12. A method of imparting flame retardancy to a thermoplastic resin composition, comprising adding about 0.1 to about 30 parts by weigh of a flame retardant represented by the following Chemical Formula 1 to about 100 parts by weight of a thermoplastic resin comprising polystyrene, styrene-acrylonitrile copolymer resin (SAN), rubber modified polystyrene resin (HIPS), rubber modified aromatic vinyl copolymer resin, ASA resin, MABS resin, polycarbonate resin, polyphenylene ether resin, polyphenylene sulfide resin, polyester resin, polyolefin resin, poly(meth)acrylate resin, polyamide resin, polyvinyl chloride resin, or a combination thereof:

[Chemical Formula 1]

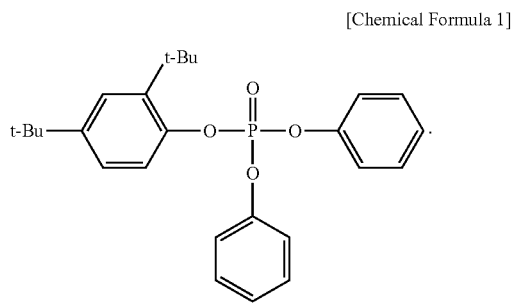

13. The method of claim 12, wherein said thermoplastic resin comprises about 70 to about 99% by weight of a rubber modified polystyrene and about 1 to about 30% by weight of a polyphenylene ether resin.

14. The method of claim 13, wherein said resin composition a flame retardancy of V-1 or V-0 measured in accordance with UL 94 using a ⅛" thick test specimen and an impact strength of about 10 to about 50 kgf·cm/cm measured in accordance with ASTM D 256 using a ⅛" notched thick test specimen.

15. The method of claim 12, wherein said thermoplastic resin is polycarbonate resin.

16. The method of claim 15, wherein said resin composition has a flame retardancy of V-0 measured in accordance with UL 94 using a ⅛" thick test specimen and an impact strength of about 58 to about 80 kgf·cm/cm measured in accordance with ASTM D 256 using a ⅛" notched thick test specimen.

17. The method of claim 12, wherein said thermoplastic resin comprises about 55 to about 90% by weight of a polycarbonate resin and about 10 to about 45% by weight of a rubber modified aromatic vinyl copolymer resin.

18. The method of claim 17, wherein said resin composition has a flame retardancy of V-1 or V-0 measured in accordance with UL 94 using a ⅛" thick test specimen and an impact strength of about 55 to about 70 kgf·cm/cm measured in accordance with ASTM D 256 using a ⅛" notched thick test specimen.

* * * * *